(12) United States Patent
Weber et al.

(10) Patent No.: US 9,820,662 B2
(45) Date of Patent: Nov. 21, 2017

(54) CATHETER SYSTEMS AND METHODS FOR DETERMINING BLOOD FLOW RATES WITH OPTICAL SENSING

(71) Applicant: BOSTON SCIENTIFIC SCIMED, INC., Maple Grove, MN (US)

(72) Inventors: Jan Weber, Maastricht (NL); James M. Anderson, Fridley, MN (US); Aiden Flanagan, Galway (IE); Eric M. Petersen, Maple Grove, MN (US); Steven R. Larsen, Lino Lakes, MN (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 484 days.

(21) Appl. No.: 14/523,506

(22) Filed: Oct. 24, 2014

(65) Prior Publication Data
US 2015/0119724 A1    Apr. 30, 2015

Related U.S. Application Data

(60) Provisional application No. 61/895,815, filed on Oct. 25, 2013.

(51) Int. Cl.
*A61B 6/00* (2006.01)
*A61B 5/026* (2006.01)
(Continued)

(52) U.S. Cl.
CPC ........ *A61B 5/0261* (2013.01); *A61B 5/02007* (2013.01); *A61B 5/6852* (2013.01);
(Continued)

(58) Field of Classification Search
CPC ........ A61B 5/0084; A61B 1/07; A61B 5/0075
(Continued)

(56) References Cited

U.S. PATENT DOCUMENTS

| 5,058,587 A | 10/1991 | Kohno et al. |
| 6,166,806 A | 12/2000 | Tjin |

(Continued)

FOREIGN PATENT DOCUMENTS

| JP | 2012501703 A | 1/2012 |
| WO | 2012164481 A1 | 12/2012 |

OTHER PUBLICATIONS

Schneditz et al., "Sound Speed, Density and Total Protein Concentration of Blood," J. Clin. Chem. Clin. Biochem, 27: 803-806, 1989.
(Continued)

*Primary Examiner* — Amanda Patton
*Assistant Examiner* — Philip C Edwards
(74) *Attorney, Agent, or Firm* — Seager, Tufte & Wickhem, LLP

(57) ABSTRACT

Catheter systems and methods for determining blood flow rates based on light reflection measurements. The catheter may include a lumen extending between a proximal end of the catheter and a distal end of the catheter. The catheter may include fluid infusion openings at the distal end region of the catheter that are configured to permit the indicator fluid to exit the catheter from the lumen. The catheter system may include an optical fiber having one or more sensors thereon for sensing light reflected by blood particles in a body vessel lumen. A blood flow rate may be determined based on the sensed light reflected by blood particles in the body vessel lumen.

16 Claims, 14 Drawing Sheets

(51) Int. Cl.
    *A61B 5/02*    (2006.01)
    *A61B 5/00*    (2006.01)
    *G01F 1/708*   (2006.01)
    *A61B 5/028*   (2006.01)
    *G01N 15/00*   (2006.01)
    *G01N 15/14*   (2006.01)

(52) U.S. Cl.
    CPC ....... G01F 1/7086 (2013.01); G01N 15/1459 (2013.01); *A61B 5/0084* (2013.01); *A61B 5/028* (2013.01); *G01N 2015/0073* (2013.01); *G01N 2015/1486* (2013.01)

(58) Field of Classification Search
    USPC ......................................................... 600/478
    See application file for complete search history.

(56) References Cited

U.S. PATENT DOCUMENTS

| | | | |
|---|---|---|---|
| 7,549,965 | B2 | 6/2009 | Krivitski et al. |
| 2004/0092830 | A1* | 5/2004 | Scott .................... A61B 5/0066 600/478 |
| 2004/0158157 | A1* | 8/2004 | Jensen .................... A61B 1/227 600/476 |
| 2005/0131284 | A1 | 6/2005 | Grinvald et al. |
| 2010/0234698 | A1 | 9/2010 | Manstrom et al. |
| 2011/0137178 | A1* | 6/2011 | Tearney ............... A61B 5/0068 600/476 |
| 2011/0238020 | A1 | 9/2011 | Goedje et al. |
| 2012/0086791 | A1 | 4/2012 | Zheng |
| 2012/0238869 | A1 | 9/2012 | Schmitt et al. |

OTHER PUBLICATIONS

Aarnoudse et al., "Direct Volumetric Blood Flow Measurement in Coronary Arteries by Thermodilution," J. Am. Coll. Cardiol, 50(24): 2294-2304, Nov. 22, 2007.

Begum et al., "Theoretical Evaluation of Ultrasonic Velocities in Binary Liquid Mixtures of Anisaldehyde with Some Alcoxyethanols at Different Temperatures," ISRN Physical Chemistry, 2012: 12 pages.

Japanese Office Action dated Mar. 14, 2017 from Japanese Patent Application No. 2016-525975.

\* cited by examiner

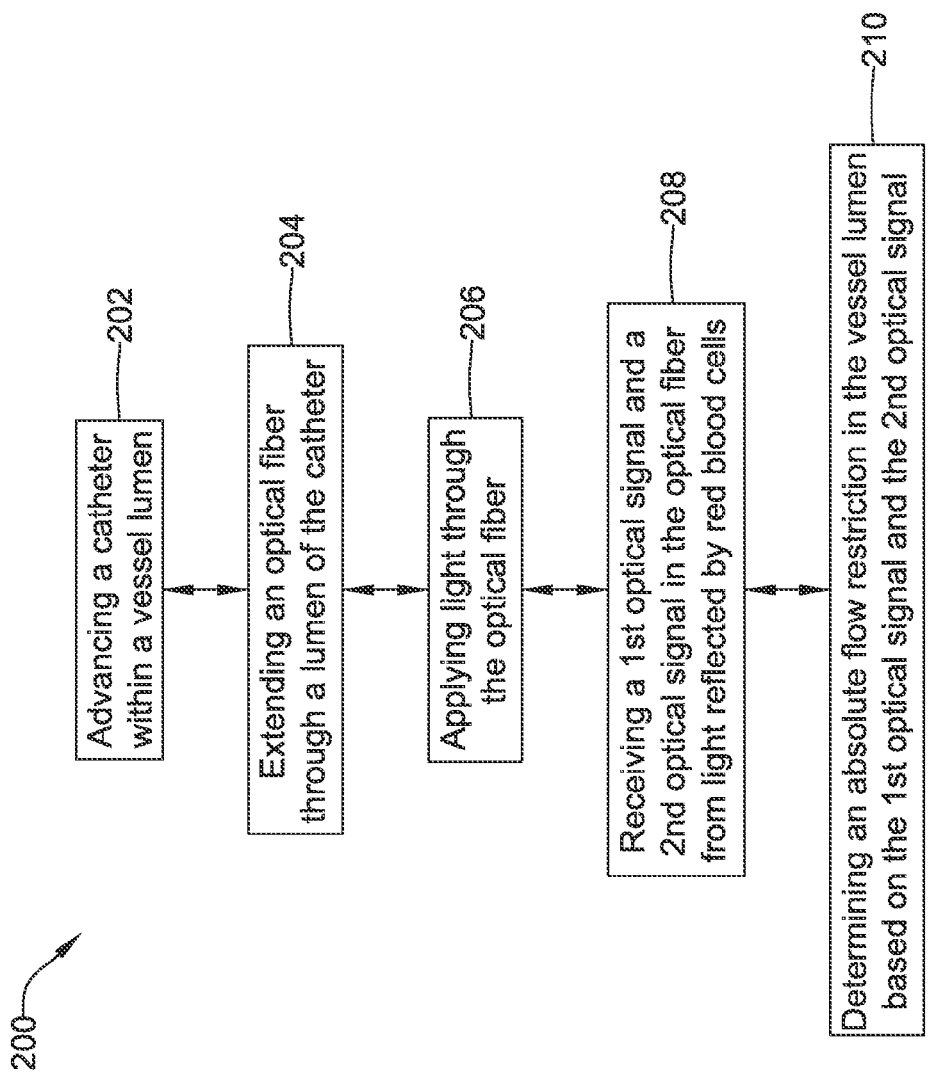

CATHETER SYSTEMS AND METHODS FOR DETERMINING BLOOD FLOW RATES WITH OPTICAL SENSING

CROSS-REFERENCE TO RELATED APPLICATIONS

This application claims priority under 35 U.S.C. §119 to U.S. Provisional Application Ser. No. 61/895,815, filed Oct. 25, 2013, the entirety of which is incorporated herein by reference.

TECHNICAL FIELD

The disclosure is directed to catheter systems and methods for determining blood flow rates in blood vessels, such as coronary arteries. More particularly, the disclosure is directed to systems and methods for determining blood flow rates based on optical measurements.

BACKGROUND

Blood flow rate measurements are taken in blood vessels, such as coronary arteries. In one blood flow rate measurement technique, Fractional Flow Reserve (FFR) may be calculated across a stenosis. FFR is defined as the ratio of the maximal blood flow achievable in a stenotic macro-vessel to the normal maximal flow in the same vessel. Such a measurement represents the fraction of the maximum flow that can be maintained despite the presence of a stenosis. In another blood flow rate measurement technique, absolute blood flow rate through a body vessel may be calculated (e.g., with a thermodilution system or method). The calculated absolute blood flow rate may be used for the diagnosis and understanding of microvascular disease.

SUMMARY

This disclosure provides design, material, manufacturing method, and use alternatives for medical devices. An example medical device may include a system for determining fluid flow rate in a body lumen. The system comprises:
  a catheter including:
  a first lumen;
  a second lumen;
  one or more fluid infusion openings in communication with the first lumen and located at a distal end region of the catheter, the one or more fluid infusion openings are configured to permit fluid to exit the catheter from the first lumen;
  one or more openings in communication with the second lumen and located at the distal end region of the catheter;
  an optical fiber having a reflective surface at a distal end thereof, wherein the optical fiber is advanceable through the second lumen of the catheter and positionable distal of the one or more openings in communication with the second lumen; and
  wherein the reflective surface is substantially transparent to one or more wavelengths of light.

Alternatively or additionally to any of the embodiments above, the optical fiber is configured to receive light reflecting from particles flowing in a body lumen.

Alternatively or additionally to any of the embodiments above, the system further comprises a beam splitter in communication with the optical fiber, wherein the beam splitter separates light reflected by the reflective surface from light reflected by particles flowing in the body lumen.

Alternatively or additionally to any of the embodiments above, the system further comprises a receiving detector for measuring reflected light received in the optical fiber.

Alternatively or additionally to any of the embodiments above, the system further comprises a Fabry-Perrot cell at the distal end of the optical fiber, wherein the reflective surface is a diaphragm of the Fabry-Perrot cell.

Alternatively or additionally to any of the embodiments above, the system further comprises a metal tube affixed to a distal end of the optical fiber and extending past a distal end of the optical fiber; and a diaphragm covering a distal opening of the metal tube.

Alternatively or additionally to any of the embodiments above, a space between the distal end of the optical fiber and the diaphragm forms a Fabry-Perrot cavity.

Alternatively or additionally to any of the embodiments above, the system further comprises one or more light reflecting surfaces positioned at a distal end of the catheter.

Alternatively or additionally to any of the embodiments above, the system further comprises one or more light reflecting surfaces positioned on a surface of the catheter defining the second lumen.

Alternatively or additionally to any of the embodiments above, the system further comprises one or more light reflecting surfaces positioned on the catheter; and wherein the one or more light reflecting surfaces are configured to reflect light having a wavelength between 620 nanometers (nm) and 740 nm.

Alternatively or additionally to any of the embodiments above, the light reflecting surfaces are positioned on the catheter at a position configured to reflect light toward the optical fiber.

An example method of measuring absolute blood flow rate in a vessel lumen comprises:
  extending an optical fiber through a vessel lumen;
  applying light through the optical fiber to red blood cells in the vessel lumen passing the distal end of the optical fiber;
  receiving an optical signal in the optical fiber from light reflected by the red blood cells; and
  determining a number of blood cells passing the optical fiber per unit time from the optical signal.

Alternatively or additionally to any of the embodiments above, the method further comprises advancing a catheter to a desired location within a vessel lumen, the catheter including a proximal end, a distal end, and a lumen extending from the proximal end through the distal end; and positioning a distal tip of the optical fiber at a position distal one or more fluid infusion openings in the catheter.

Alternatively or additionally to any of the embodiments above, the method further comprises dispersing a fluid into the vessel lumen at a known flow rate.

Alternatively or additionally to any of the embodiments above, the method further comprises obtaining a first measure of a number of red blood cells passing the optical fiber per unit time when fluid is dispersed into the vessel lumen at a first known flow rate; and obtaining a second measure of the number of red blood cells passing the optical fiber per unit time when fluid is dispersed into the vessel lumen at a second known flow rate.

Alternatively or additionally to any of the embodiments above, the method further comprises determining a measure of a number of red blood cells passing the optical fiber per unit time when no fluid is dispersed into the vessel lumen based on the first measure of the number of red bloods cells passing the optical fiber per unit time and the second measure of the number of red blood cells passing the optical fiber per unit time.

Alternatively or additionally to any of the embodiments above, determining the measure of the number of red blood cells passing the optical fiber per unit time when no fluid is dispersed into the vessel lumen includes linearly extrapolating from data points based on the first measure of the number of red blood cells, the first known flow rate, the second measure of the number of red blood cells, and the second known flow rate.

Alternatively or additionally to any of the embodiments above, the determined measure of the number of red blood cells passing the optical fiber per unit time when no fluid is dispersed into the vessel lumen is an absolute blood flow rate in the vessel lumen.

Alternatively or additionally to any of the embodiments above, the dispersed fluid is saline.

Alternatively or additionally to any of the embodiments above, the dispersed fluid is devoid of blood particles.

Another example method of identifying absolute flow restriction in a vessel lumen comprises:

extending an optical fiber through a vessel lumen to a target location;

applying light through the optical fiber to a diaphragm at a distal end of the optical fiber, wherein the diaphragm reflects a first optical signal that is dependent on a pressure in the vessel lumen and allows light reflectable by red blood cells in the vessel lumen to pass therethrough;

receiving in the optical fiber the first optical signal and a second optical signal that is produced from light reflected by the red blood cells; and determining an absolute flow restriction in the vessel lumen based on the received first optical signal and the received second optical signal.

Alternatively or additionally to any of the embodiments above, the method further comprises measuring a number of red blood cells passing the optical fiber per unit time from the second optical signal.

Alternatively or additionally to any of the embodiments above, the optical fiber includes a Fabry-Perrot cell at the distal end thereof and the diaphragm forms a distal end of the Fabry-Perrot cell.

Alternatively or additionally to any of the embodiments above, the method further comprises determining an absolute blood flow rate in the vessel lumen from the second optical signal.

Another example method comprises:

extending a elongate tubular member through a tubular lumen;

extending an optical fiber through the tubular lumen;

applying light through the optical fiber to particles in the tubular lumen passing the distal end of the optical fiber;

receiving an optical signal in the optical fiber from light reflected by the particles; and dispersing a fluid from the elongate tubular member into the tubular lumen at a known flow rate.

Alternatively or additionally to any of the embodiments above, the method further comprises advancing the elongate tubular member to a desired location within the tubular lumen, the elongate tubular member including a proximal end, a distal end, and a lumen extending from the proximal end through the distal end; and positioning a distal tip of the optical fiber at a position distal one or more fluid infusion openings in the elongate tubular member.

Alternatively or additionally to any of the embodiments above, the method further comprises obtaining a first measure of a number of particles passing the optical fiber per unit time when fluid is dispersed into the tubular lumen at a first known flow rate; and obtaining a second measure of the number of particles passing the optical fiber per unit time when fluid is dispersed into the tubular lumen at a second known flow rate.

Another example system comprises:

a catheter including:

a first lumen;

a second lumen;

one or more fluid infusion openings in communication with the first lumen and located at a distal end region of the catheter, the one or more fluid infusion openings are configured to permit fluid to exit the catheter from the first lumen;

one or more openings in communication with the second lumen and located at the distal end region of the catheter;

an elongate member having one or more light emitters and one or more light detectors at a distal end thereof, wherein the elongate member is advanceable through the second lumen of the catheter and positionable distal of the one or more openings in communication with the second lumen; and wherein the one or more light emitters are configured to emit light onto particles in the body lumen and the one or more light detectors are configured to detect light reflected by particles in the body lumen.

The above summary of some embodiments is not intended to describe each disclosed embodiment or every implementation of the aspects of the disclosure. The Figures, and Detailed Description, which follow, more particularly exemplify these embodiments.

BRIEF DESCRIPTION OF THE DRAWINGS

The aspects of the disclosure may be more completely understood in consideration of the following detailed description of various embodiments in connection with the accompanying drawings, in which:

FIG. 14 is a schematic flow diagram depicting an illustrative method of determining blood flow restriction within a body vessel.

Figure 1:
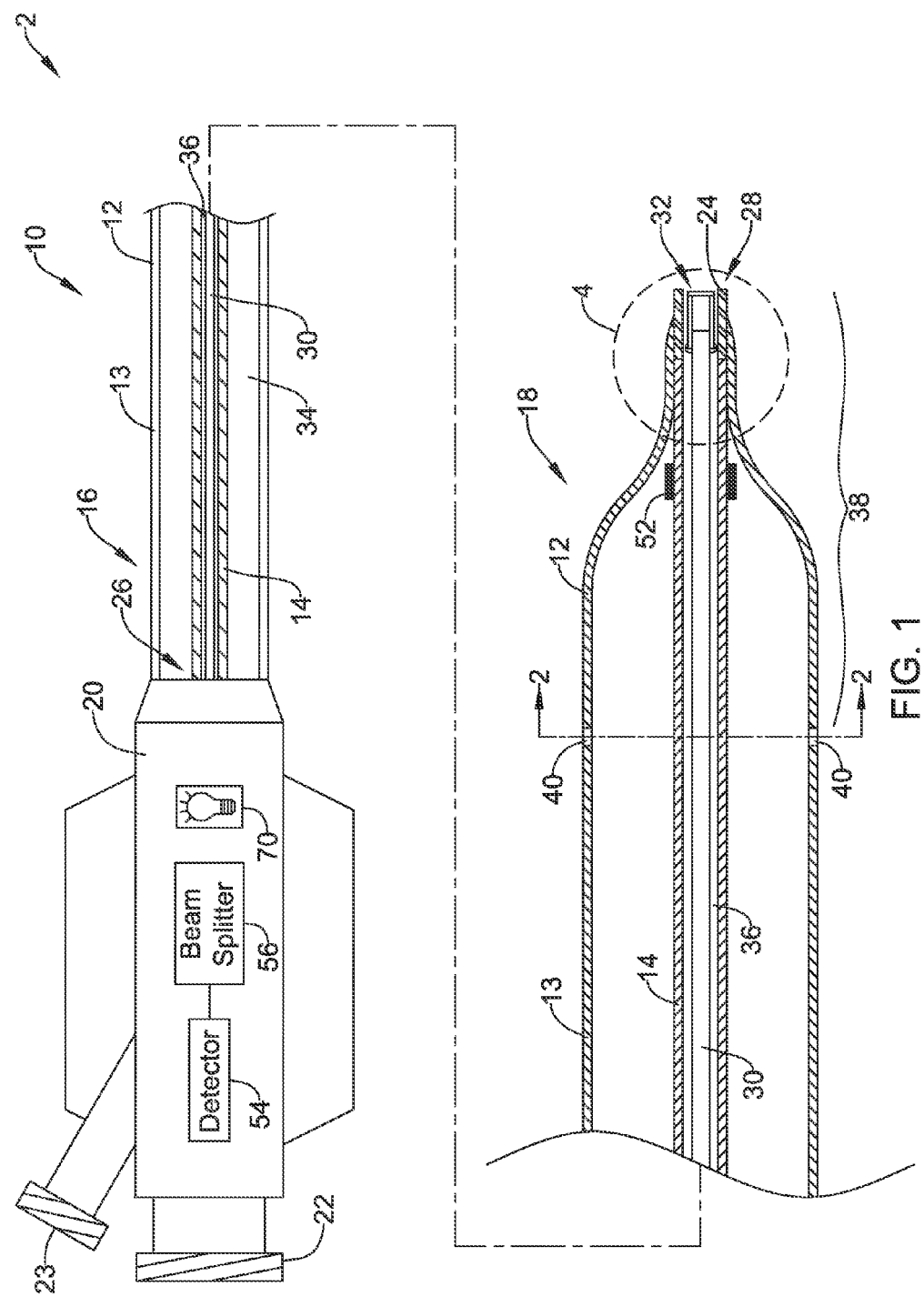
FIG. 1 is a schematic partial sectional view of an illustrative catheter system including an infusion catheter and associated optical fiber for determining blood flow rates through a body vessel.

While the aspects of the disclosure are amenable to various modifications and alternative forms, specifics thereof have been shown by way of example in the drawings and will be described in detail. It should be understood, however, that the intention is not to limit aspects of the disclosure to the particular embodiments described. On the contrary, the intention is to cover all modifications, equivalents, and alternatives falling within the spirit and scope of the disclosure.

DETAILED DESCRIPTION

For the following defined terms, these definitions shall be applied, unless a different definition is given in the claims or elsewhere in this specification.

All numeric values are herein assumed to be modified by the term "about", whether or not explicitly indicated. The term "about" generally refers to a range of numbers that one of skill in the art would consider equivalent to the recited value (i.e., having the same function or result). In many instances, the term "about" may be indicative as including numbers that are rounded to the nearest significant figure.

The recitation of numerical ranges by endpoints includes all numbers within that range (e.g., 1 to 5 includes 1, 1.5, 2, 2.75, 3, 3.80, 4, and 5).

Any relative terms, such as first, second, third, right, left, bottom, top, etc., used herein in connection with a feature are just that and are not meant to be limiting other than to be indicative of the relative relationship of the modified feature with respect to another feature.

Although some suitable dimensions, ranges and/or values pertaining to various components, features and/or specifications are disclosed, one of skill in the art, incited by the present disclosure, would understand desired dimensions, ranges and/or values may deviate from those expressly disclosed.

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

The following detailed description should be read with reference to the drawings in which similar elements in different drawings are numbered the same. The detailed description and the drawings, which are not necessarily to scale, depict illustrative embodiments and are not intended to limit the scope of the disclosure. The illustrative embodiments depicted are intended only as exemplary. Selected features of any illustrative embodiment may be incorporated into an additional embodiment unless clearly stated to the contrary.

Typically, coronary muscles are supplied with blood flowing through a macro-vascular bed and an adjacent micro-vascular bed. In the macro-vascular bed, Fractional Flow Reserve (FFR) may be used to better understand macro-vascular disease and the flow rate across a stenosis in a body vessel. For the diagnosis and understanding of microvascular disease, FFR is not useful.

Rather than using FFR, absolute blood flow rate measurements may be utilized for the diagnosing and understanding of microvascular diseases. From a calculated absolute blood flow rate, the absolute resistance in a body vessel may be determined (assuming absolute pressure is known or can be determined). For example, when the flow rate of the blood has been calculated and the pressures proximal ($P_p$) and distal ($P_d$) of the stenosis have been calculated (e.g., from the use of an FFR wire, a Fabry-Perrot sensor, Fiber-Bragg sensor, or other pressure sensor), the resistance of the stenosis or narrowing of the body vessel 80 can be calculated with the following equation:

$$R_s = (P_p - P_d)/Q_b.$$

Where:
$R_s$=resistance across the stenosis or narrowing
$P_d$=measured pressure distal of the stenosis or narrowing
$P_p$=measured pressure proximal of the stenosis or narrowing
$Q_b$=the actual blood flow rate.

Thus, the measured actual blood flow rate, as well as other calculated parameters, may be useful for the diagnosis and understanding of a number of pathophysiological conditions such as heart transplantation, stem cell therapy, a transmural myocardial infarction, etc., for example.

In one example, thermo-dilution methods and/or systems (e.g., taking temperatures within a body vessel before and/or after a blood flow is diluted with an infusion fluid) may be used to determine absolute blood flow rates in a body vessel. Thermo-dilution methods, however, are based on the assumption that the temperature of a mixed fluid is not rising when one measures temperature distal to a catheter tip. Such an assumption, however, is only true when one measures a temperature close enough to the catheter tip so that temperature does not start rising after being cooled down with an infusion fluid. As it is desirable to have a certain amount of mixing between the infusion fluid and blood in a body vessel, it may be desirable to take measurements at a far enough distance from the distal tip of the catheter to ensure adequate mixture between the infusion fluid and the blood in the body vessel, which is at odds with taking measurements close to the distal tip of a catheter to ensure a temperature of the flow is not rising.

As disclosed herein, it is possible to determine pressure and absolute blood flow rate within a body vessel by optical means of measuring both pressure and absolute flow rate using an optical fiber (e.g., a single optical fiber). In some instances, a Fabry-Perrot cell or Fiber Bragg Grating (FBG) with a partially reflective end surface (e.g., diaphragm or mirror, hereinafter referred to as a reflective surface, mirror, grating, etc.) may be used at a distal end of the optical fiber to facilitate sensing pressure and absolute blood flow rate within a body vessel.

Pressure sensing and/or temperature sensing may be performed with optical sensing techniques. In one illustrative example, a fiber with an optical sensor (e.g., a Fabry-Perrot sensor) thereon may be used to sense pressure (e.g., sense pressures within a body vessel) and/or temperature (e.g., sense temperatures within a body vessel). Structurally, a Fabry-Perrot optical sensor may form a cavity at an end of an optical fiber, where a tube (e.g., a glass tube, a metal tube, etc.) is affixed or otherwise connected to an end of the tube and a membrane (e.g., a diaphragm or mirror) is connected to the end of the tube to form a cavity defined by the end of the optical fiber, the tube, and the membrane (e.g., a flexible membrane).

In operation, a light may be passed through the optical fiber and some of the light will reflect on the end of the optical fiber and some of the light will pass to the membrane and reflect on the membrane. The reflected light may pass back through the optical fiber to a detector. As the membrane bends inwards or outwards due to pressure changes and/or temperature changes about the optical sensor, interference patterns between the light reflected at a proximal side of the cavity (e.g., at a distal end of the optical fiber) and the light reflected at the distal side of the cavity (e.g., at the membrane) may change as an effect of the change in length of the cavity, where the change and/or interference patterns are indicative of sensed pressures and/or temperatures.

In some instances, a similar optical fiber or optical sensor system may be utilized to sense reflective images of an optical beam sent into a volume of streaming blood and measure a scattering of blood cells passing by in the measurement volume over a particular time domain. As a result, the number of blood cells or particles passing by an optical sensor may be counted over a period of time and an absolute blood flow rate may be determined.

In some instances, pressure and temperature may be sensed with a single Fabry-Perrot cell. To facilitate sensing pressure and/or temperature, the tube and/or the membrane may be made at least partially from pressure sensitive materials and/or temperature sensitive materials. Illustrative pressure sensitive materials may include, but are not limited to, polyvinylidene fluoride (PVDF), polypropylene (PP), polyethylene (PE), polyvinyl alcohol (PVA), polyimide films (e.g., KAPTON®), biaxially oriented polyethylene terephthalate (PET) (e.g., mylar), silicone, parylene, etc., and/or any combination thereof. Illustrative temperature sensitive materials may include, but are not limited to, solids, liquids, gasses, polyesters, PET, PVA, nylon, polyvinyl chloride (PVC), aluminum, conductor doped membranes (e.g., silver, carbon-urethane, etc.), etc., and/or any combination thereof. Further, the membrane of the Fabry-Perrot cell may be made from a material that is partially reflective and allows some wavelengths of light to pass therethrough (e.g., partially transparent) in order to facilitate determining an absolute blood flow rate with the optical sensor.

An illustrative catheter system 2 including an infusion catheter 10 and associated optical fiber 30 (e.g., a single or a plurality of elongate members or elongate fibers) for determining blood flow rates through a body vessel and/or other measurements (e.g., pressure, temperature, etc.) in the body vessel using an optical measurement technique is illustrated in FIG. 1. The infusion catheter 10 may include an elongate catheter shaft 12 extending distally from a hub assembly 20. The catheter shaft 12 may have a proximal end 16 attached to the hub assembly 20 and a distal end 18 opposite the proximal end 16. The catheter shaft 12 may be a dual lumen catheter shaft having a first lumen 34 (e.g., an infusion lumen (FIG. 1) or a fiber or guidewire lumen) and a second lumen 36 (e.g., a fiber or guidewire lumen (FIG. 1) or an infusion lumen) extending along at least a portion of the catheter shaft 12. Alternatively, the catheter shaft 12 may have a single lumen or more than two lumens. In one example of a catheter shaft 12, the catheter 10 may be an over-the-wire (OTW) catheter in which the second lumen 36 may extend through the entire length of the catheter shaft 12 from the distal end 18 to the proximal end 16, as shown in FIG. 1. However, in other embodiments, the catheter 10 may be a single-operator-exchange (SOE) catheter in which the second lumen 36 extends only through a distal portion of the catheter shaft 12.

The hub assembly 20 may include a first proximal port 22 in fluid communication with the first lumen 34 and a second proximal port 23 in optical communication with the second lumen 36. Alternatively, or in addition, the first proximal port 22 and/or the second proximal port 23 may be in one or more other types of communication with the first lumen 34 and/or the second lumen 36. A source of infusion fluid (not shown), such as an infusion pump, syringe, etc., may be coupled to the first proximal port 22 to supply infusion fluid to the first lumen 34. A controller and/or source of light (not shown) may be coupled to the second proximal port 23 to supply light to the optical fiber 30 and/or the second lumen 36 for use in taking measurements with an optical sensor 32. Alternatively, or in addition, the controller and/or source of light may be located within the hub assembly 20 or along the catheter 10 or optical fiber 30 (which may be located within a body vessel 80 when in operation). In some instances, a light may be generated by pressing, selecting, or touching a light actuator 70 on the hub assembly 20, a light actuator on a remote light producing device (not shown), a light actuator on a controller (not shown) separate from the hub assembly 20, and/or on any other device in communication with the light producing device. Illustrative light sources may include, but are not limited to, light emitting diodes (LEDs), piezoelectric generated lights, white band light sources (e.g., white band light sources that may be directly coupled to a fiber), lasers, etc.

In some instances, the catheter shaft 12 may include an outer tubular member 13 and an inner tubular member 14 extending through the lumen of the outer tubular member 13, where the inner tubular member 14 may define the second lumen 36. With the OTW catheter construction of FIG. 1, the first lumen 34 may be defined between an outer surface of the inner tubular member 14 and an inner surface of the outer tubular member 13 throughout the catheter shaft 12. In instances in which the catheter 10 has an SOE construction, the first lumen 34 may be defined by the outer tubular member 13 through the proximal portion of the catheter shaft 12, while the first lumen 34 may be defined between an outer surface of the inner tubular member 14 and an inner surface of the outer tubular member 13 through the distal portion of the catheter shaft 12. In other instances, the catheter shaft 12 may define the first lumen 34 and the second lumen 36 such that the first lumen 34 and the second lumen 36 have elongated portions extending along the catheter shaft 12 substantially parallel to one another. Alternatively, the catheter shaft 12 may define a single lumen (e.g., the first lumen 34) acting as the infusion fluid lumen and the optical fiber lumen or the guidewire lumen.

As referred to above, the lumen of the inner tubular member 14 may define the second lumen 36 with a distal port 28 (e.g., a distal optical fiber port or guidewire port) proximate the distal end of the inner tubular member 14 and a proximal port 26 (e.g., a proximal optical fiber port or guidewire port) proximate the proximal end of the inner tubular member 14. The distal port 28 may be located proximate the distal end 18 of the catheter shaft 12 and the proximal port 26 may be located proximate the proximal end 16 of the catheter shaft 12 (e.g., with an OTW catheter construction) or a short distance proximal of the distal end 18 and distal of the proximal end 16 of the catheter shaft 12 (e.g., with an SOE catheter construction). The proximal port 26 may be of any desired construction, providing access to the second lumen 36. In some instances, the proximal port 26 of a catheter with an SOE construction may be formed in accordance with a guidewire port forming process as described in U.S. Pat. No. 6,409,863, which is incorporated herein by reference.

A distal end portion 38 of the outer tubular member 13 or catheter shaft 12 may have at least a portion that is a reduced diameter portion or necked portion. In some instances, the distal end portion 38 may be secured to the inner tubular member 14 to seal the first lumen 34 proximate the distal end 18 of the catheter shaft 12. For example, the distal end portion 38 may include a tapered region in which the outer tubular member 13 or catheter shaft 12 tapers down to a reduced diameter at the distal end of the outer tubular member 13. In some instances, the inner surface of a distal end portion of the outer tubular member 13 may be secured to the outer surface of a distal end portion of the inner tubular member 14 in the distal end portion 38 of the catheter 10. The outer tubular member 13 may be secured to the inner tubular member 14 or other feature, for example, by laser welding, hot jaws, or other thermal bonding method, an adhesive bonding method, or other bonding method if desired.

In some instances, the catheter shaft 12 may include a distal tip 24, formed as a separate component and secured at the distal end 18 of the catheter shaft 12. For example, in some instances the distal tip 24 may be secured to the inner tubular member 14, outer tubular member 13, or other portion of the catheter shaft 12, for example, by laser welding, hot jaws, or other thermal bonding method, an adhesive bonding method, or other bonding method if desired. As shown in FIG. 1, in some embodiments, the distal end portion of the outer tubular member 13 may span a joint between the inner tubular member 14 and the distal tip 24 such that the distal end portion of the outer tubular member 13 is bonded to each of the inner tubular member 14 and the distal tip 24. In other instances, the distal tip 24 may be formed as a unitary portion of the inner tubular member 14, the outer tubular member 13, or other portion of the catheter shaft 12.

The catheter shaft 12 may also include one or more radiopaque markers 52 located proximate the distal end 18 of the catheter shaft 12. The radiopaque marker(s) 52 may facilitate viewing the location of the distal end 18 of the catheter shaft 12 using a fluoroscopy technique or other visualization technique during a medical procedure. In one illustrative instance, the catheter shaft 12 may include a radiopaque marker 52 secured to the inner tubular member 14 proximate the tapered distal end portion 38 of the catheter shaft 12, as shown in FIG. 1.

The catheter shaft 12 may include one or more fluid infusion openings 40 (e.g., holes, apertures, etc.) located at a distal end region of the catheter 10. The fluid infusion openings 40 may be in fluid communication with the first lumen 34 and may be configured to permit infusion fluid F to exit the catheter 10 from the first lumen 34 proximate the distal end 18 of the catheter shaft 12. For example, the fluid infusion openings 40 may be configured to expel an infusion fluid F (e.g., saline) in one or more radially outward directions from each of the fluid infusion openings 40 to facilitate mixing of the infusion fluid with blood flowing through the vessel lumen. Alternatively, or in addition, the fluid infusion openings 40 may be arranged in a different orientation, such as in different fashions to permit infusion fluid F to be expelled generally distally from the catheter shaft 12.

Figure 2:
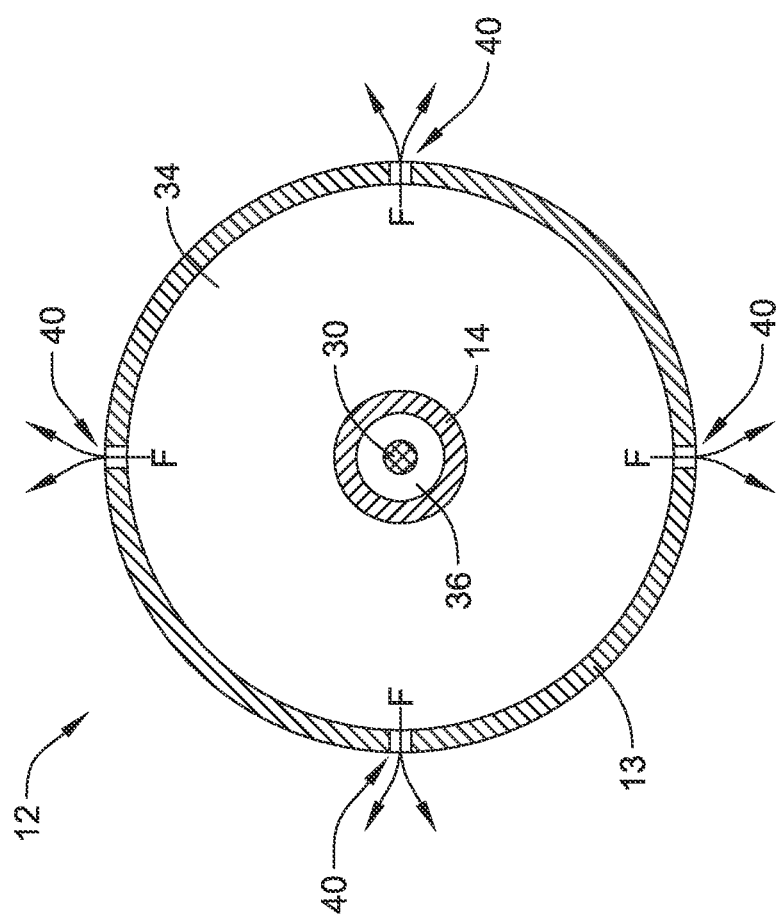
FIG. 2 is a schematic cross-sectional view taken along line 2-2 of FIG. 1.

The catheter shaft 12 may include a plurality of fluid infusion openings 40 extending through a wall of the outer tubular member 13 from an inner surface of the outer tubular member 13 to an outer surface of the outer tubular member 13. As shown in FIG. 2 which is a schematic cross-sectional view taken along line 2-2 in FIG. 1, in one illustrative embodiment, the catheter shaft 12 may include four fluid infusion openings 40 equidistantly and circumferentially spaced around the outer tubular member 13 (e.g., with each fluid infusion opening 40 arranged about 90° from another fluid infusion opening 40). In other embodiments, the catheter shaft 12 may include one, two, three, or more fluid infusion openings 40 arranged around the perimeter of the catheter shaft 12 in any manner.

Figure 3:
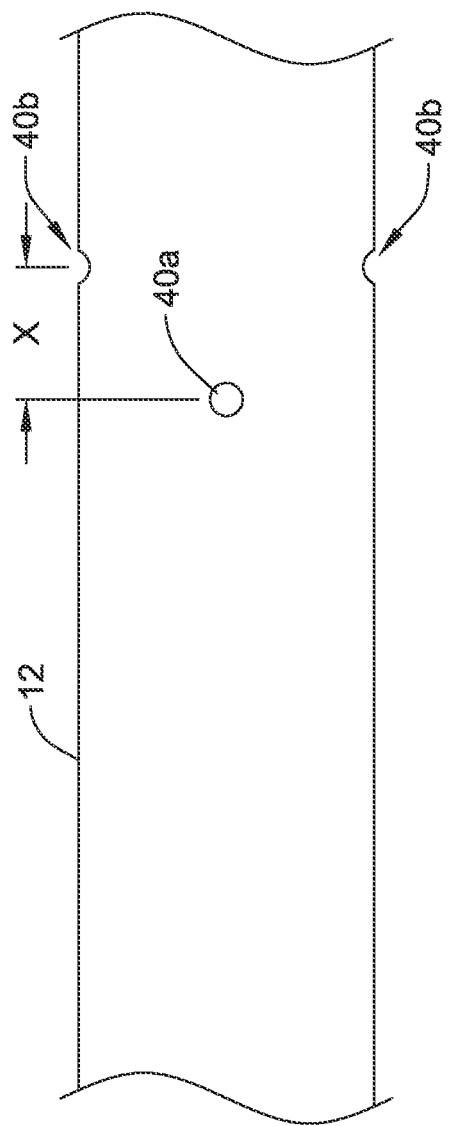
FIG. 3 is a schematic side view of a portion of an illustrative infusion catheter.

As shown in FIG. 3, in some instances one or more of the fluid infusion openings 40 may be longitudinally displaced along the catheter shaft 12 from one or more of the other fluid infusion openings 40. For example, first and second oppositely positioned fluid infusion openings 40a (only one of which is visible in FIG. 3) may be located a longitudinal distance X, such as about 0.5 millimeters, about 1 millimeter, about 2 millimeters, or about 3 millimeters, away from third and fourth oppositely positioned fluid infusion openings 40b, in some embodiments. In other instances, the first and second oppositely positioned fluid infusion openings 40a may be longitudinally aligned with the third and fourth oppositely positioned fluid infusion openings 40b, if desired.

The one or more fluid infusion openings 40 may be configured to generate a jet of infusion fluid F exiting the catheter shaft 12, as referred to above. For example, the fluid infusion openings 40 may be appropriately sized to generate a pressure stream of the infusion fluid F exiting the fluid infusion openings 40. In some instances, the fluid infusion openings 40 may have a diameter of about 25 microns (0.025 millimeters) to about 300 microns (0.300 millimeters), about 25 microns (0.025 millimeters) to about 100 microns (0.100 millimeters), about 100 microns (0.100 millimeters) to about 200 microns (0.200 millimeters), or about 200 microns (0.200 millimeters) to about 300 microns (0.300 millimeters), for example. The size of the fluid infusion openings 40 may be selected based on the volume of infusion fluid to ensure a jet of infusion fluid is formed exiting the catheter shaft 12.

Figure 4:
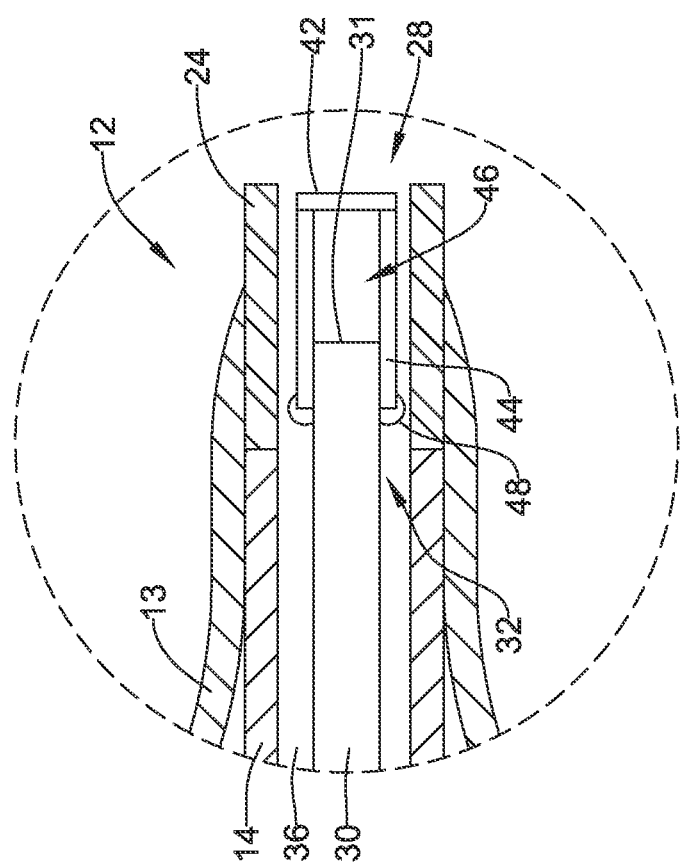
FIG. 4 is a schematic cross-sectional view of the illustrative catheter system of FIG. 1, taken along dotted circle 4.

FIG. 4 is an enlarged schematic view of the features of circle 4 at the distal end 18 of the catheter system 2 in FIG. 1. Within circle 4, an optical sensor 32 may be formed at or about the distal end 31 of the optical fiber 30 extending through the second lumen 36 of the catheter shaft 12. The optical fiber 30 may be positioned within the second lumen 36 such that it may be advanced through an opening in communication with the second lumen and extend through the outer surface of the catheter shaft 12 (e.g., distal port 28).

The optical sensor 32 may be any type of optical sensor 32 capable of reflecting light and/or receiving reflected light and being used to determine an absolute flow rate through a body vessel, while, in some cases, capable of being used to also detect pressure within the body vessel. In one example, the optical sensor 32 may include a reflective surface 42 (e.g., a mirror, diaphragm, membrane, and/or any at least partially reflective surface) at a distal end of the optical fiber 30 advanceable through the second lumen 36 and positionable distal of the distal port 28. The reflective surface 42 may be made from any material. In one example, the reflective surface 42 may be made from a material capable of reflecting at least a first portion of wavelengths that pass through a distal end 31 of the optical fiber 30 and allow a second portion of wavelengths of light that pass through the distal end 31 of the optical fiber 30 to pass therethrough.

The reflective surface 42 or mirror may reflect any set of wavelengths and allow any set of wavelengths to pass through. The wavelengths of light that the reflective surface 42 or mirror may allow to pass therethrough may be at least wavelengths of light that blood particles reflect (e.g., wavelengths associated with the color red, for example, wavelengths between about 620 nm and 740 nm, where visible red light may have a wavelength of about 650 nm). In some cases, the wavelengths of light that the reflective surface 42 or mirror may reflect may include some or all visible light wavelengths other than the wavelengths between about 620 nm and 740 nm. Although the examples of this disclosure pertain primarily to applications directed toward visible light, the reflective surface 42 may reflect wavelengths and/or let wavelengths pass through, where the wavelengths are wavelengths associated with gamma ray waves, X ray waves, UV waves, visible light waves, infrared waves, microwaves, FM waves, AM waves, and/or long radio waves.

In some instances, the reflective surface 42 (e.g., a partially reflective membrane or diaphragm) may be separated from the distal end 31 of the optical fiber 30. In one illustrative example, a tube 44 may be connected to a distal end region of the optical fiber 30 such that the tube 44 may extend distal of the distal end 31 of the optical fiber 30. The reflective surface 42 may be affixed to a distal end of the tube 44 and spaced from the distal end 31 of the optical fiber 30. The distal end 31 of the optical fiber 30, the tube 44, and the reflective surface 42 may form or define a cavity 46 (e.g., a Fabry Perrot cavity).

The tube 44 may be affixed to the optical fiber 30 in any manner. For example, the tube 44 may be affixed to the optical fiber 30 with a joining material 48 (e.g., a biocompatible adhesive, solder, or other joining material). The tube 44 may be made from any biocompatible material. For example, the tube may be made from a glass material (e.g., a including silicon dioxide), a metal material (e.g., a material including stainless steel), or any other material or combination of materials.

In some instances, the optical sensor 32 shown in FIG. 4 may be configured to sense pressure along with sensing blood flow rates within a body vessel. The reflective surface 42 may be made from a pressure sensitive material, which may result in the reflective surface 42 deflecting inward or outward in response to fluctuations in pressure. In response to deflections of the reflective surface 42, the distance between the distal end 31 of the first portion 30a of the optical fiber 30 and the reflective surface 42 may change and cause changes in interference patterns of light reflected by the distal end 31 of the optical fiber 30 and light reflected by the reflective surface 42 (e.g., changes in optical signal reflected through the optical fiber 30), where these changes may be indicative of a sensed pressure. Illustrative pressure sensitive materials may include, but are not limited to, polyvinylidene fluoride (PVDF), polypropylene (PP), polyethylene (PE), polyvinyl alcohol (PVA), polyimide films (e.g., KAPTON®), biaxially oriented polyethylene terephthalate (PET) (e.g., mylar), silicone, parylene, gold, silver, copper, grapheme, etc., and/or any combination thereof.

Figure 5:
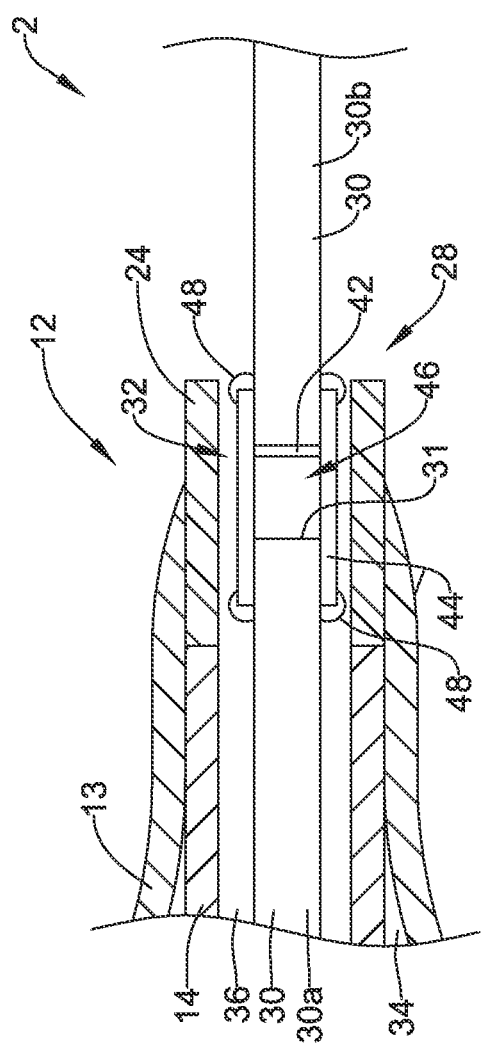
FIG. 5 is a schematic cross-sectional view of a distal end of an illustrative catheter system including an infusion catheter and associated optical fiber for determining blood flow rates through a body vessel.

FIG. 5 is a schematic partial cross-sectional view of a catheter system 2 having a catheter 10 and an optical fiber 30 with an optical sensor 32 attached thereto, where the catheter 10 may include the first lumen 34 and the second lumen 36, and the optical fiber 30 extends through the second lumen 36 and extends out of the distal port 28 (e.g., out the opening extending between the second lumen 36 and the outer surface of the catheter shaft 12 at the distal end 18 of the catheter shaft 12).

The optical sensor 32 of FIG. 5 may include a tube 44 affixed to a first portion 30a of the optical fiber 30 and a second portion 30b of the optical fiber 30 forming and/or defining the cavity 46 (e.g., a Fabry-Perrot cavity or other cavity). The reflective surface 42 may be positioned within the cavity at a proximal end of the second portion 30b of the optical fiber 30. As discussed above, the reflective surface 42 may reflect a first portion of wavelengths of light passing through the distal end 31 of the first portion 30a of the optical fiber 30, while allowing a second portion of wavelengths to pass therethrough for reflection on blood particles within the a body vessel.

In some instances, the optical sensor 32 shown in FIG. 5 may be configured to sense temperature along with sensing blood flow rates within a body vessel. The reflective surface 42 may be made from a temperature sensitive material, which may result in the reflective surface 42 deflecting inward or outward in response to fluctuations in temperature. In response to deflections of the reflective surface 42, the distance between the distal end 31 of the first portion 30a of the optical fiber 30 and the reflective surface 42 may change and cause changes in interference patterns of light reflected by the distal end 31 of the optical fiber 30 and light reflected by the reflective surface 42 (e.g., changes in optical signal reflected through the optical fiber 30), where such changes may be indicative of a sensed temperature.

Any material with a relatively high thermal expansion coefficient may be considered a temperature sensitive material. Illustrative temperature sensitive materials may include, but are not limited to, solids, liquids, gasses, polyesters, PET, PVA, nylon, polyvinal chloride (PVC), aluminum, conductor doped membranes (e.g., silver, carbon-urethane, etc.), etc., and/or any combination thereof. For transparent materials, glass ($Sio_2$) has a reasonably high thermal expansion coefficient. In some cases, a particularly temperature sensitive design for the reflective surface 42 may include having two layers (e.g., one glass layer and one polymer layer) that sandwich a layer of liquid (e.g., ethanol or other liquid or gas having a very high coefficient of thermal expansion and that may be sensitive to relatively small changes in temperature). In some alternative or additional instances, a thermochromic material or dye may be coated on the reflective surface 42 (e.g., liquid crystals may be formed on the reflective surface 42), such that the color of the reflective surface 42 or thermochromic material or die will change with a small temperature change. The change in color of the reflective surface 42 or thermochromic material or die may be detected with spectral reflectance measurement optical fiber 30 and/or optical sensor 32.

Figure 6:
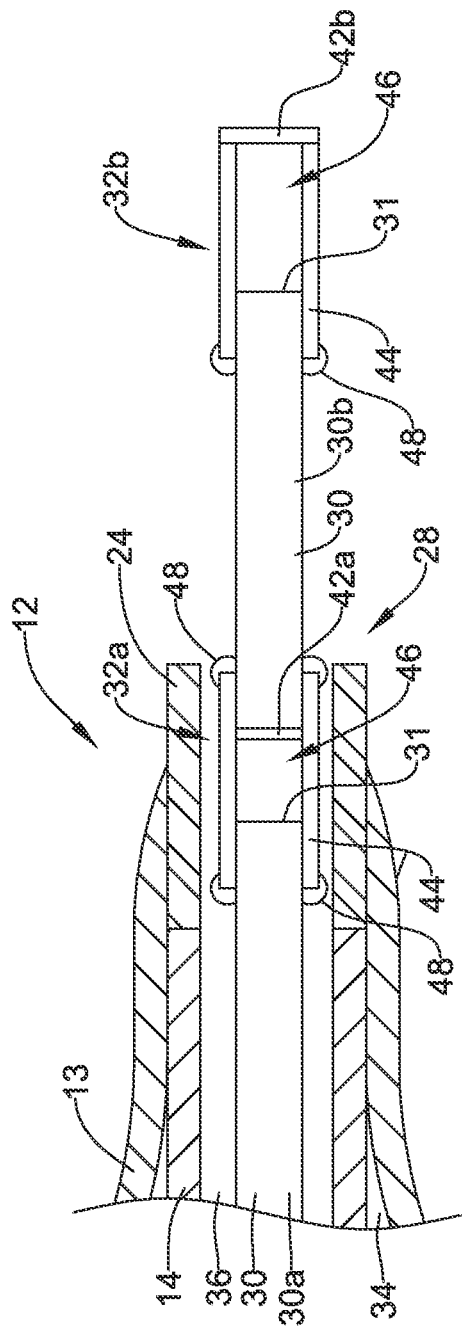
FIG. 6 is a schematic cross-sectional view of a distal end of an illustrative catheter system including an infusion catheter and associated optical fiber for determining blood flow rates through a body vessel.

The catheter system 2 may include a catheter 10 and an optical fiber 30 that is capable of sensing pressure, temperature, and flow rates through a body vessel. As shown in FIG. 6, optical sensors 32, as described herein, may be stacked on top of one another along the optical fiber 30 such that a first optical sensor 32a may be capable of sensing temperature and a second optical sensor 32b may be capable of sensing pressure, while each optical sensor 32a and 32b may allow wavelengths of light reflectable by blood particles to pass through the reflective surfaces 42 thereof. In one example, the first optical sensor 32a may include a reflective surface 42a of a temperature sensitive material enclosed within a cavity 46 defined by a first portion 30a of the optical fiber 30, a second portion 30b of the optical fiber 30 and the tube 44. In the example, a second optical sensor 32b configured to sense pressure may be positioned along the optical fiber 30 distal of the first optical sensor 32a configured to sense temperature. The second optical sensor 32b configured to sense pressure may include a reflective surface 42b supported at a distance away from the distal end 31 of the optical fiber 30 by a tube 44 attached to the distal end portion of the second portion 30b of the optical fiber 30. Both the first optical sensor 32a configured to sense temperature and the second optical sensor 32b configured to sense pressure may allow wavelengths of light capable of reflecting on blood particles to pass therethrough. Such a combined sensor as shown in FIG. 6 may operate in a manner similar to the optical sensors 32 disclosed in the FIGS. 4 and 5.

Figure 7:
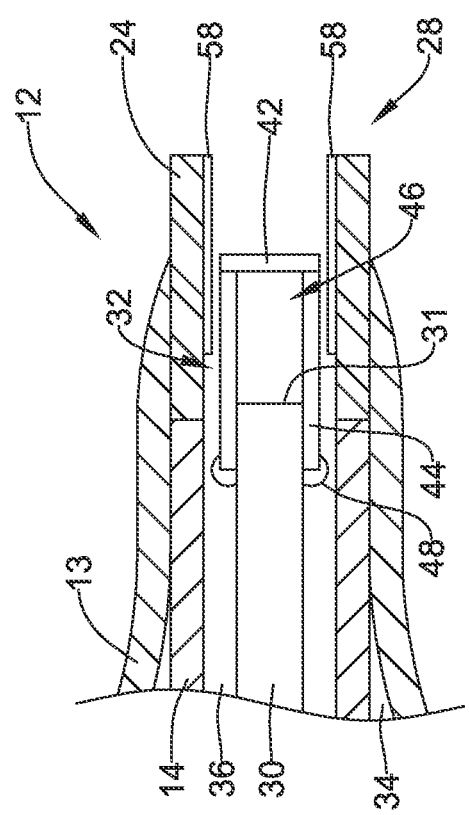
FIG. 7 is a schematic cross-sectional view of a distal end of an illustrative catheter system including an infusion catheter and associated optical fiber for determining blood flow rates through a body vessel.

In some instances the catheter 10 may be configured to facilitate directing light sent through the optical fiber 30 or other light carrying and/or emitting device toward blood or blood particles in a body vessel and/or facilitate directing light reflected from the blood or blood particles back to the optical fiber 30 or other light carrying and/or detecting device. As shown in FIG. 7, the catheter 10 may include one or more reflective surfaces 58 (e.g., a light reflecting surface) on a surface at the distal end 18 of the catheter 10 defining the second lumen 36 (e.g., a guidewire lumen, optical fiber lumen, or other lumen). For example, the one or more reflective surfaces 58 may be located on a surface of the distal tip 24, on the distal end of the inner tubular member 14, and/or on one or more other portions of the catheter 10 adjacent a light emitting portion of the optical fiber 30 and blood or blood particles in a body vessel.

Illustratively, the reflective surfaces 58 may be configured at a distal end 18 of the catheter 10 such that light reflected from blood or blood particles reflects on the reflective surfaces 58 and is directed back into and/or through the optical fiber 30 for detection by the detector 54. The reflective surfaces 58 may facilitate providing a stronger reflected light signal or beam to the detector 54 through the optical fiber 30, or to and/or through another detector mechanism, by reflecting more of the light reflected by blood or blood particles into the optical fiber 30 than would be reflected without the reflective surfaces 58. As biological material may not be a good reflector of light, the stronger reflected light signal may result in better detection of blood particles per unit time.

The reflective surface 58 may be configured to reflect light having wavelengths between about 620 nm and 740 nm and/or configured to reflect light having any other wavelengths. The reflective surfaces 58 may be configured from any type of material capable of at least reflecting light having wavelengths between about 620 nm and 740 nm. The reflective surfaces 58 may be formed on and/or attached to the catheter 10 in any manner, including, but not limited to, through polishing, through adhesive connections, through welding connections, and/or through other forming and/or attaching techniques.

Figure 8:
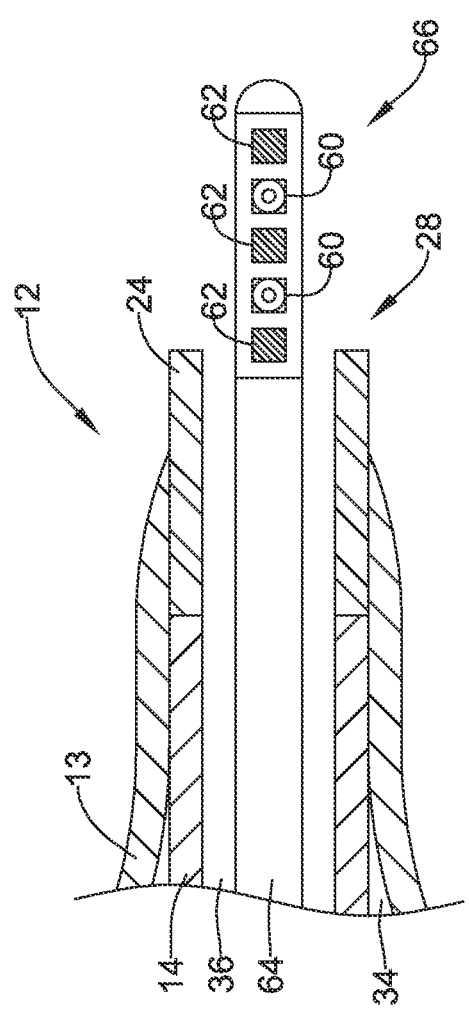
FIG. 8 is a schematic cross-sectional view of a distal end of an illustrative catheter system including an infusion catheter and associated optical sensor for determining blood flow rates through a body vessel.

In some instances, a distal light source 60 and/or a distal light detector 62 may be utilized in the catheter system 2. As shown in FIG. 8, a guidewire 64 or other elongate member configured to extend through the catheter 10 (e.g., a guide catheter, a wire, etc.) may include one or more light sources 60 (e.g., light emitters) and one or more light detectors 62 positioned on and/or at a distal end 66 of the guidewire 64. The light sources 60 and light detectors 62 may be in electrical communication with and/or may be operationally controlled by a controller at the hub assembly 20 or a controller in communication with the hub assembly 20. The light sources 60 and light detectors 62 may be the types described herein and/or may be any other type of light source and/or light detector.

Any number of light sources 60 and/or any number of light detectors 62 may be utilized. These light sources 60 and/or light detectors 62 may be arranged in any manner, where the arrangement may be configured to direct light from the light sources 60 onto blood or blood particles in a body vessel and the light detectors 62 may be configured to detect or capture light reflected by the blood or blood particles in the body vessel.

In one example of utilizing distally position light sources 60 and light detectors 62, the distal end 66 of the guidewire 64 or other elongate member may include three light detectors 62 and two light sources 60 positioned between the light detectors 62, where the light detectors 62 and the light sources 60 may be longitudinally displaced from one another, as shown in FIG. 8. Although the light sources 60 and the light detectors 62 may take a rectangular form in FIG. 8, the light sources 60 and the light detectors 62 may take on one or more other shapes, including but not limited to circular shapes, ring shapes surrounding the guidewire 64, etc., as desired.

Figure 9:
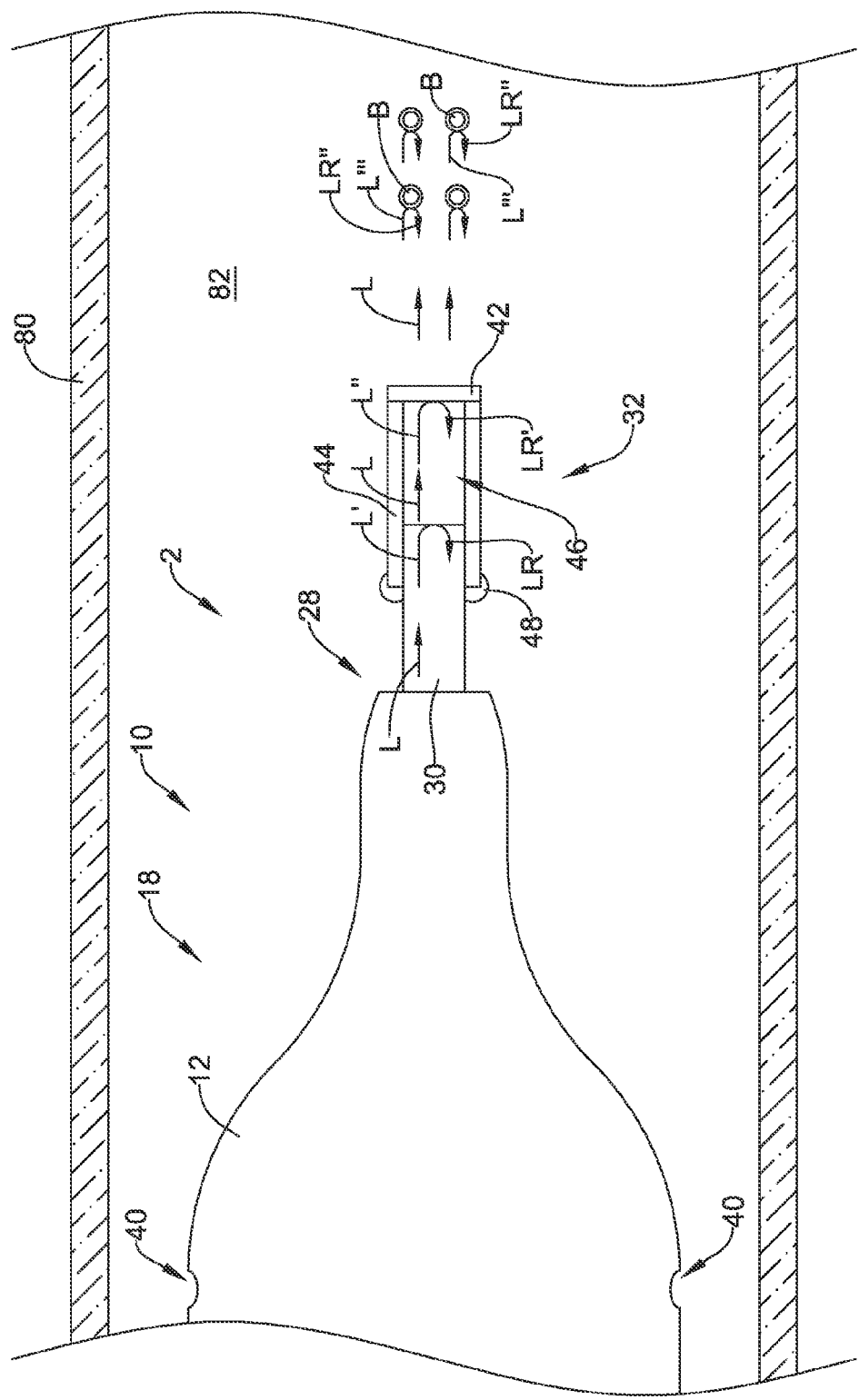
FIG. 9 is a schematic view of the illustrative catheter system depicted in FIG. 1 while partially positioned within a vessel lumen of a body vessel, where an optical sensor is schematically shown in a cross-sectional view.
Figure 10:
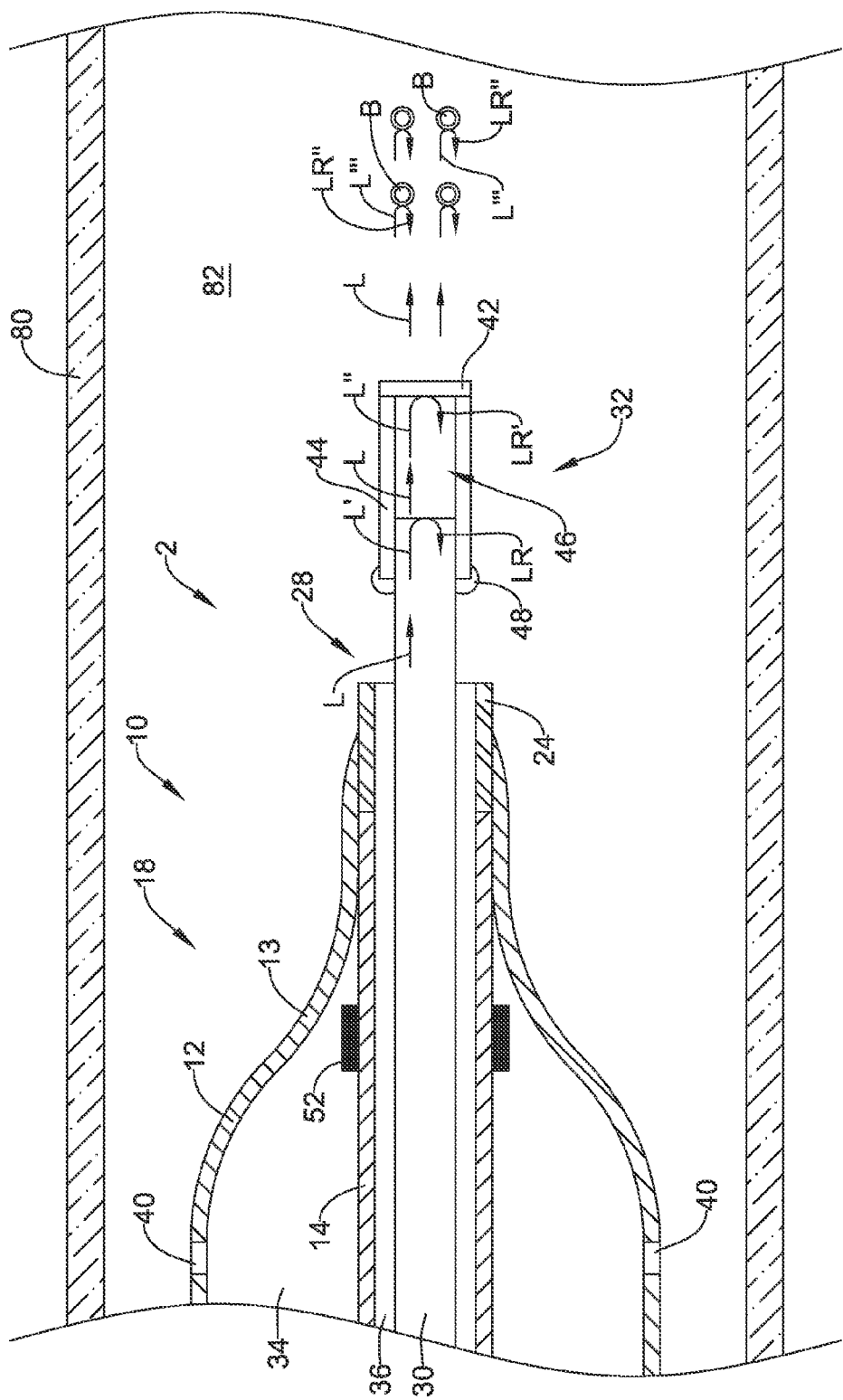
FIG. 10 is a schematic cross-section view of the illustrative catheter system depicted in FIG. 1 while partially positioned within a vessel lumen of the body vessel.
Figure 11:
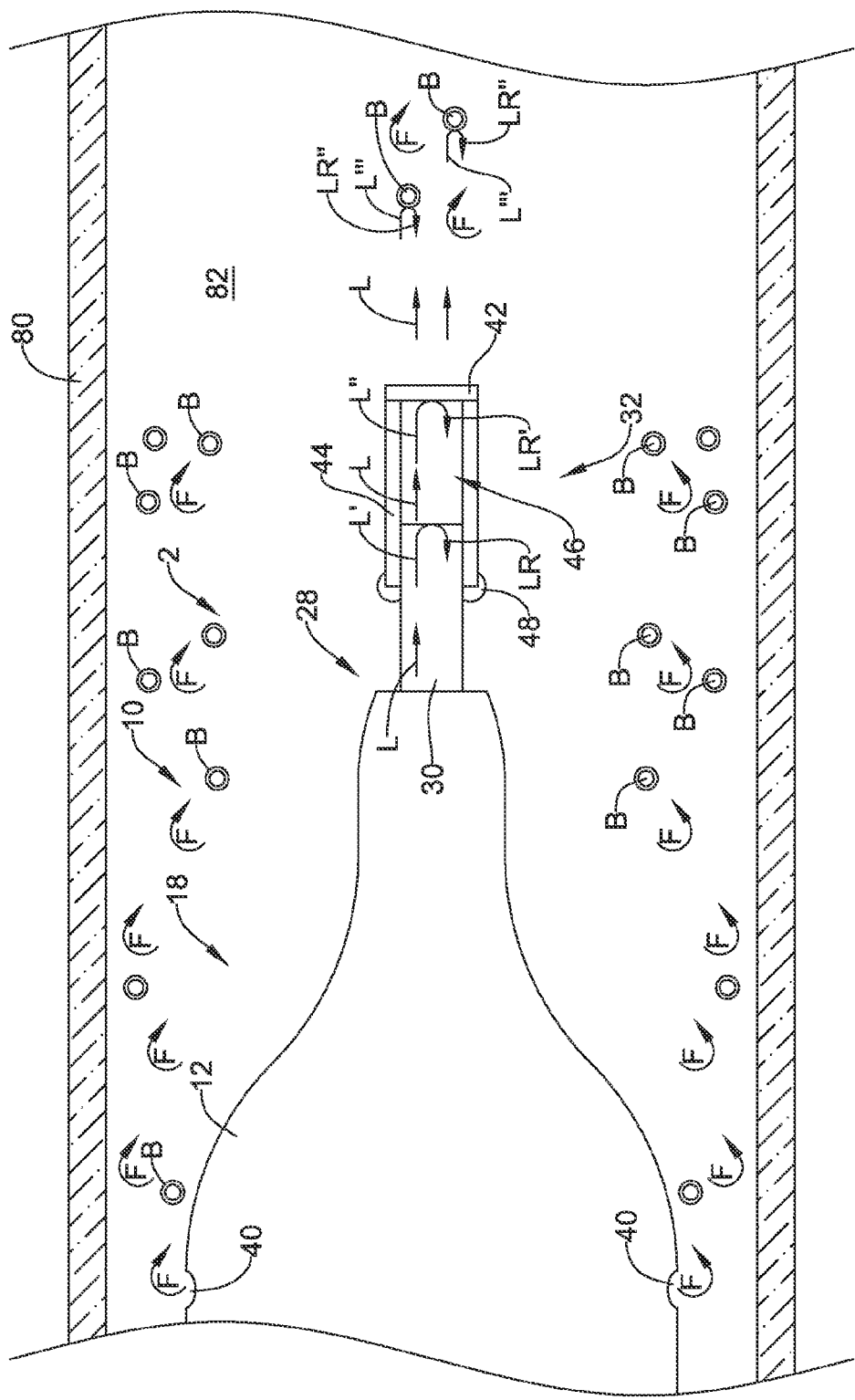
FIG. 11 is the schematic view of the illustrative catheter system depicted in FIG. 9, where infusion fluid is dispersed from the illustrative catheter system.

FIGS. 9-11 depict an illustrative catheter system 2 positioned within a lumen 82 of a body vessel 80. A beam of light L may be sent through the optical fiber 30 starting at a proximal end of the optical fiber 30. In one example, a light actuator 70 at the hub assembly 20 (as shown in FIG. 1), a light actuator connected to the catheter system 2, or any other light actuator may be used to actuate the light beam into and through the optical fiber 30.

As shown in FIGS. 9 and 10, a catheter 10 may be positioned within a lumen 82 of a body vessel 80 (e.g., at a target location) and the optical sensor 32 may extend through the distal port 28 to a position within the lumen 82 distal of the distal port 28. A light beam L may be sent through the optical fiber 30 to and/or through a distal end thereof. A first portion L' of the light beam L may reflect on the distal end 31 of the optical fiber 30 and form a first reflected light signal LR that may be sent through the optical fiber 30 to the hub assembly 20 or controller connected to the hub assembly 20, where the hub assembly 20 may include a detector 54 and/or a beam splitter 56 for splitting or separating reflected light beams traveling through the optical fiber, for detecting reflected light beams from the respective reflective surfaces, and for calculating one or more measurements based on the reflected light signals. A second portion L" of the light beam L that passes through the distal end 31 of the optical fiber 30 may reflect on the reflective surface 42 and form a second reflected light signal LR' that may be sent through the optical fiber 30 to the hub assembly 20 and/or to a controller connected to the hub assembly 20 for separation from other light signals traveling through the optical fiber 30 (e.g., by the beam splitter 56) and/or detection by the detector 54. A third portion L''' of the light beam L that passes through the distal end 31 of the optical fiber 30 and the reflective surface 42 may reflect on blood particles B in the flow passing the optical sensor 32 and form a third reflected light signal LR" that may be sent through the optical fiber 30 to the hub assembly 20 or controller connected to the hub assembly 20 for separation from other light signals by the beam splitter 56 and/or for detection by the detector 54.

In some instances, an infusion fluid F may be expelled or dispersed into the vessel lumen 82 of the body vessel 80 to facilitate taking measurements at different temperatures, pressures and/or flow rates of fluid passing through the vessel lumen 82. As shown in FIG. 11, infusion fluid F (e.g., saline or other material essentially devoid of particles) may be dispersed from the fluid infusion openings 40 at a distal end portion 38 of the catheter 10 (e.g., from the first lumen 34), such that the infusion fluid F may mix with the blood B in the vessel lumen 82. As a result of the mixing between the infusion fluid F with the blood B and the formed diluted flow, the temperature, the pressure, and/or the flow rate of fluid in the vessel lumen 82 may change over time. Through the optical sensing discussed above with respect to at least FIGS. 9 and 10, and discussed further below, the temperature, the pressure and/or the flow rate of fluid in the vessel lumen 82 and changes thereof may be calculated or determined over time.

Figure 12:
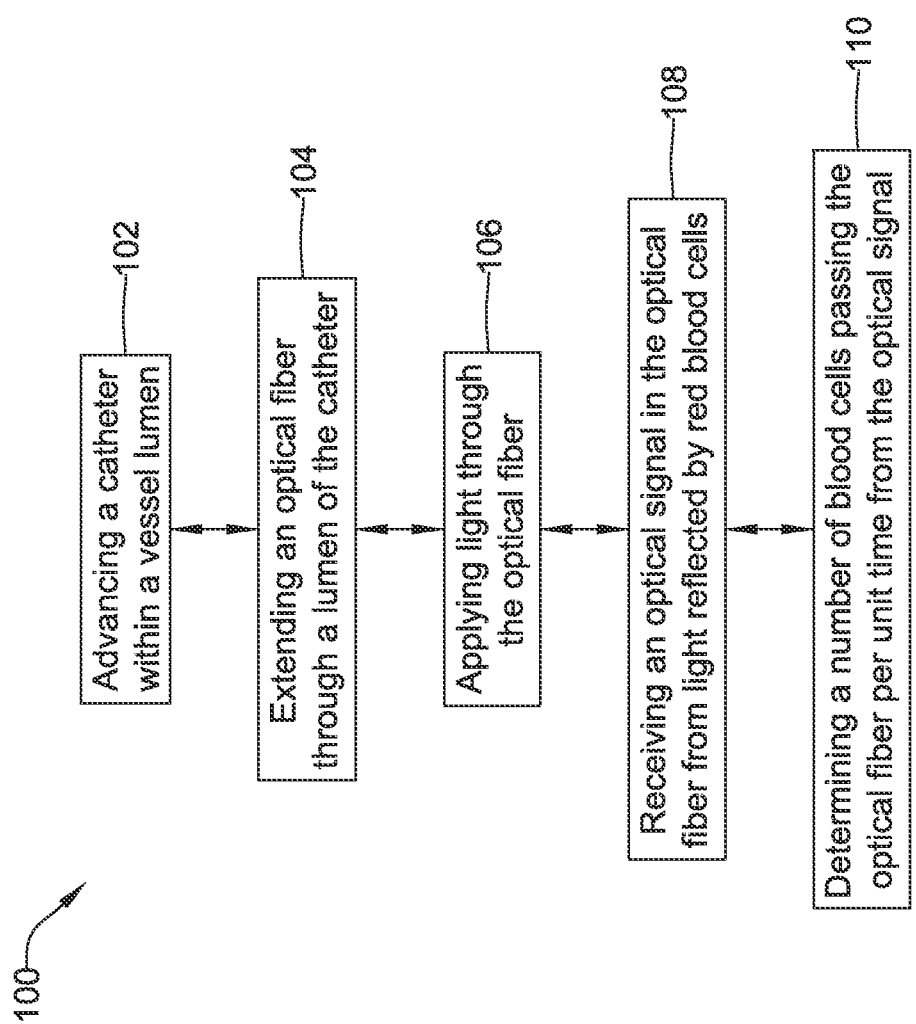
FIG. 12 is a schematic flow diagram depicting an illustrative method of determining blood flow rate through a body vessel.

In operation, a method 100 of measuring absolute blood flow in a vessel lumen is disclosed, as shown in the illustrative flow diagram of FIG. 12. For example, in the method 100, a catheter 10 may be advanced 102 to a desired location within a vessel lumen 82. The catheter 10 may be any type of catheter, for example, the catheter 10 may be a catheter similar to the catheters disclosed herein including a proximal end 16, a distal end 18, and a lumen (e.g., first lumen 34 and/or second lumen 36) extending from the proximal end 16 through the distal end 18. An optical fiber 30 may be extended 104 through the lumen (e.g., the second lumen 36, as shown in the Figures). In some instances, a distal tip or distal end 31 of the optical fiber 30 or a distal end of the optical sensor 32 may be positioned at a position distal one or more of the fluid infusion openings 40 in the catheter 10.

A light L may be applied 106 through the optical fiber 30 to the blood B (e.g., red blood cells or red blood particles) in the vessel lumen 82, where the light L (e.g., a portion L" of light L or other portion) passes through the distal end 18 of the catheter 10. In response to applying light through the optical fiber 30 to the blood B, an optical signal may be received 108 in the optical fiber 30 from, or of light reflected by, the blood B in the vessel lumen 82 (e.g., reflected light LR", as shown in FIGS. 9-11). The optical signal of the reflected light LR" from the blood B in the vessel lumen 82 may be utilized to determine 108 a number of blood cells or particles passing the optical fiber 30 or optical sensor 32 per unit time. Illustratively, the absolute flow rate of fluid within the vessel lumen may be calculated from the determined number of blood cells or particles passing the optical fiber per unit time.

In one illustrative example, the number of blood cells or particles passing the optical fiber 30 per unit time may be determined through digital measurement. With digital measurement, in the time domain of the measurement, one may see a scattering of blood cells passing by the optical fiber 30 in the vessel lumen 82. If a threshold for a light level indicating reflected light from a blood cell or particle is established according to the light level in the digital image of the time domain, it is possible to obtain a digital "black and white" signal of light reflected by a blood cell or particle in the vessel lumen 82. The digital black and white signal may allow a count of the number of red blood cells or particles passing the optical fiber 30 and/or optical sensor 32 per unit of time. Although an amount of red blood cells or particles between individuals may differ, a count may still be meaningful with respect to the absolute flow rate within the vessel lumen 82 because the amount of red blood cells or particles may typically stay constant or relatively constant during a relative small period of time needed for a measurement period (e.g., less than one hour, about one hour, etc.).

As referred to above, fluid F may be injected or dispersed into the vessel lumen 82 through the fluid infusion opening(s) 40. In some instances, fluid F may be injected or dispersed into the vessel lumen 82 at one or more known or established flow rates. In one example, a fluid F may be injected or dispersed into the vessel lumen 82 at a first known flow rate at first time and a second known flow rate at a second time, where the first known flow rate and the second known flow rate may be similar or different and the first time and the second time are different times. A first measure of the number of red blood cells or particles passing the optical fiber 30 or optical sensor 32 per unit time may be taken when the fluid F is dispersed into the vessel lumen 82 at the first known flow rate. A second measure of the number of red blood cells or particles passing the optical fiber 30 or optical sensor 32 per unit time may be taken when the fluid F is dispersed into the vessel lumen 82 at the second known flow rate. The first measure of the number of red blood cells or particles passing the optical fiber 30 or optical sensor 32 per unit time and the second measure of the number of red blood cells or particles passing the optical fiber 30 or optical sensor 32 per unit time may be identified and/or stored in the detector 54 in the hub assembly 20 and/or in a controller (not shown) in communication with the hub assembly 20.

From the first measure of the number of red blood cells or particles passing the optical fiber 30 or optical sensor 32 per unit time and/or the second measure of the number of red blood cells or particles passing the optical fiber 30 or the optical sensor 32 per unit time, it may be possible to determine a measure of the number of red blood cells or particles passing the optical fiber per unit time when no infusion fluid F is dispersed into the vessel lumen 82 from the catheter 10 (e.g., the known flow rate of the fluid dispersed into the vessel lumen equals zero). Such a determined number of red blood cells or particles passing the optical fiber 30 or optical sensor 32 per unit time when the flow rate of the infusion fluid F is zero may be an absolute blood flow rate in the vessel lumen 82. In one example, determining the number of red blood cells or particles passing the optical fiber 30 or optical sensor 32 per unit time when no fluid is dispersed into the vessel lumen 82 from the catheter 10 may include linearly extrapolating from data points based on the first measure of the number of red blood cells, the first known flow rate, the second measure of the number red blood cells, and/or the second known flow rate.

Figure 13:
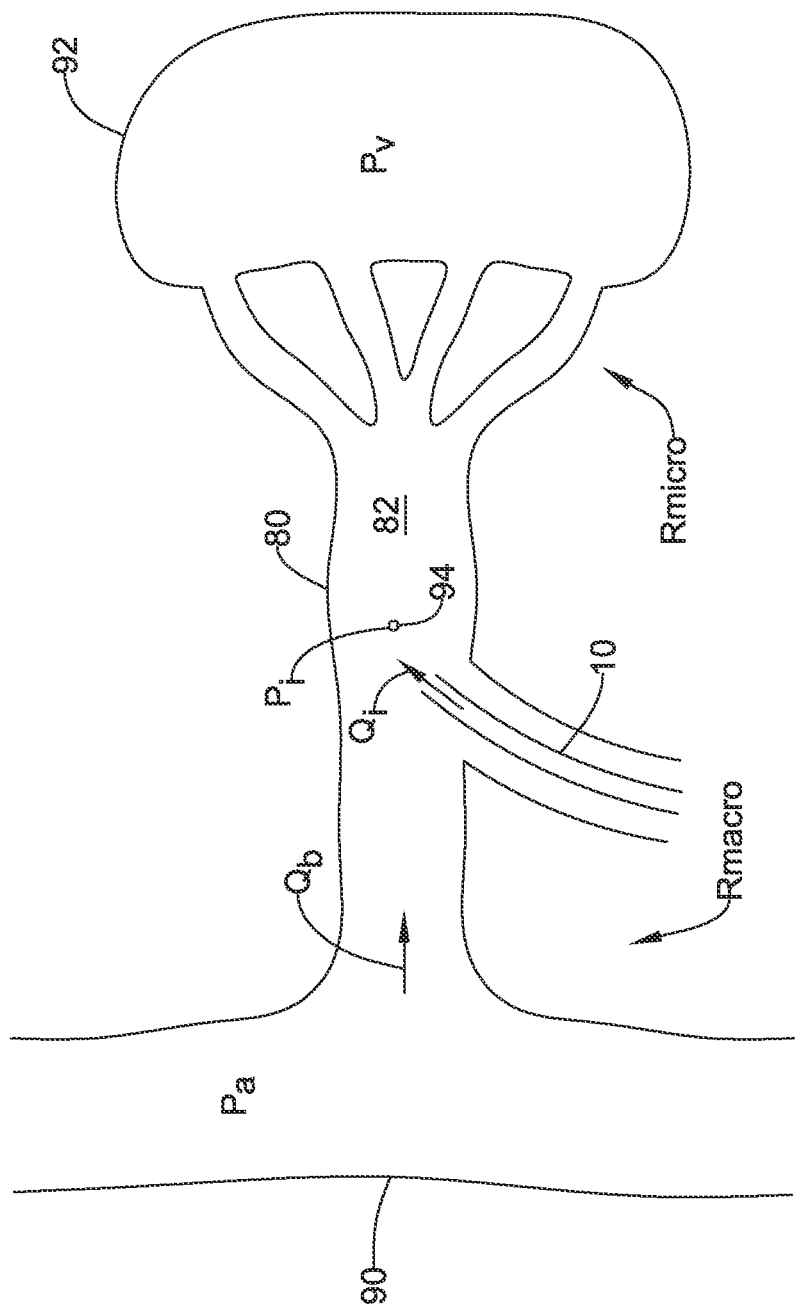
FIG. 13 is a schematic view of illustrative body vessels with an illustrative catheter inserted therein.

As infusion fluid F has no red blood cells or particles and a pressure $P_i$ at an infusion point 94, as shown in the schematic of FIG. 13, increases resulting in a lower flow rate of blood B from the aorta 90, there is a decrease in the, and potentially changing, number of red blood cells per unit volume about the optical fiber or optical sensor (not shown in FIG. 13) within the vessel lumen 82 when infusion fluid F is dispersed into the vessel lumen 82. As a result, data of red blood cells or particles passing the optical fiber or optical sensor versus infusion fluid F flow rates may be plotted and extrapolated to determine an absolute blood flow rate within the vessel lumen. Although the infusion catheter 10 is shown in FIG. 13 as entering the body vessel 80 through a vessel separate from the aorta 90, the infusion catheter may alternatively, or in addition, enter the body vessel 80 through the aorta 90 (e.g., via the femoral artery or other artery).

Flow rates of fluid within a vessel lumen 82 may be linearly related to the flow rate $Q_i$ of infusion fluid injected into the vessel lumen 82. As shown in FIG. 13, in typical body vessel systems, the aorta 90 may have a pressure $P_a$ and a related macro-bed resistance $R_{macro}$, while the venous system 92 may have a pressure $P_v$ and a related micro-bed resistance $R_{micro}$. The absolute flow rate of fluid (e.g., blood) through the body vessel 80 is $Q_b$. The flow rate of an infusion fluid F from the catheter 10 at an infusion point 94 is $Q_i$. A pressure at the infusion point 94 is $P_i$. Using an analogy from electrical calculations, the following equations hold for flow:

$$(Q_b + Q_i)^* R_{micro} = P_i - P_v, \text{ and}$$

$$Q_b^* R_{macro} = P_a - P_i.$$

Furthermore:
$P_v$ (the venous pressure) is considered to be near zero, such that $P_1 - P_v \cong = P_i$, and
$P_a$ (the pressure in the aorta) is considered to be constant (a constant average over a cardiac cycle).
As a result, the following equation also holds:

$$Q_{b(Qi)} = P_a/(R_{macro} + R_{micro}) - Q_i^*(R_{micro})/(R_{macro} + R_{micro}) = \alpha - \beta^* Q_i.$$

From this $Q_{b(Qi)} = \alpha - \beta^* Q_i$ equation, it can be seen that the flow rate $Q_i$ of an infusion fluid F dispersed into a vessel lumen 82 may be linearly related to the absolute flow rate of blood $Q_b$. Thus, it is possible to determine the required absolute flow rate of blood $Q_{b(Qi=0)}$ based on data points of measurements of a number of red blood cells or particles passing the optical fiber 30 or optical sensor 32 per unit time for two or more different flow rates $Q_i$ of an infusion fluid F dispersed into the vessel lumen 82.

In one example of determining an absolute flow rate of blood $Q_b$ based on data points (e.g., graphically determined and/or determined from fitting an equation to the data points), a first data point or a first measure of a number of red blood cells passing an optical fiber 30 or optical sensor 32 per unit time when infusion fluid F is injected into the vessel lumen 82 at a first known flow rate may be determined. In the example, a second data point or a second measure of a number of red blood cells passing the optical fiber 30 or optical sensor 32 per unit time when infusion fluid F is injected into the vessel lumen 82 at a second known flow rate may be determined. Then, a data point of a number of red blood cells passing the optical fiber 30 or optical sensor 32 per unit time when no infusion fluid F is injected into the vessel lumen 82 based on the first measure and the second measure may be determined. In one illustrative instance, the measure of a number of red blood cells passing the optical fiber 30 or optical sensor 32 per unit time when no infusion fluid F is injected into the vessel lumen 82 may include linearly extrapolating from data points based on the first measure, the first known flow rate, the second measure, and/or the second known flow rate. In such instances, the data point of a number of red blood cells passing the optical fiber 30 or optical sensor 32 when no infusion fluid F is injected into the vessel lumen 82 may be the absolute blood flow rate in the vessel lumen.

In operation, a method 200 of measuring absolute flow restriction in a vessel lumen 82 is disclosed, as shown in the illustrative flow diagram of FIG. 14. For example, a catheter 10 may be advanced 202 to a desired location within a vessel lumen 82. The catheter 10 may be any catheter 10, for example, any catheter 10 disclosed herein. Illustratively, the catheter 10 may include a proximal end 16, a distal end 18, and a lumen 34 or 36 extending from the proximal end 16 through the distal end 18. An optical fiber 30 may be advanced or extended 204 through the lumen 34 or 36 of the catheter 10, out an opening in the catheter 10 (e.g., at distal end of 18 of the catheter 10 through a distal port 28).

A light may be applied 206 through the optical fiber 30 to a diaphragm or reflective surface 42 at or adjacent a distal end 31 of the optical fiber 30. The diaphragm or reflective surface 42 may reflect first optical signal(s) that are dependent on a pressure in the vessel lumen and may allow light reflectable by red blood cells B in the vessel lumen 82 to pass therethrough. The first optical signal and a second optical sign that is produced from light reflected by the red blood cells or particles B may be received 208 in the optical fiber 30 and delivered to a controller or detector 54 and/or a beam splitter 56. The second signal received may be used to measure a number of red blood cells passing the optical fiber per unit time, as disclosed herein. An absolute blood flow restriction in the vessel lumen 82 may then be determined 210 from the received first optical signal and the received second optical signal. In one example, the pressures in a body vessel may be determined from the first signal(s) (e.g., reflected light LR') and the absolute blood flow rate $Q_b$ may be determined calculated from the second signal(s) (e.g., reflected light LR") as discussed herein or in any other manner, and the absolute flow restriction with a vessel lumen 82 may be determined from the following equation discussed above: $R_s = (P_p - P_d)/Q_b$, where $R_s$=resistance across the stenosis or narrowing or absolute flow restriction in a vessel lumen 82, $P_d$=measured pressure distal of the stenosis or narrowing, and $P_p$=measured pressure proximal of the stenosis or narrowing.

Although the systems and methods described herein are primarily described with respect to blood and body vessels, the system 2 may be utilized in other medical related methods and/or in non-medical related methods. For example, the system 2 may be utilized in a non-medical related method to determine an absolute flow rate in any tubular lumen and/or to determine an absolute flow restriction in any tubular lumen, where the tubular lumen carries a flow of fluid (e.g., a flow of gas or liquid). Illustratively, an elongate tubular member and/or an optical fiber may be extended through a tubular lumen (e.g., a vessel, a pipe, etc.) to a target location, where a distal tip or other portion of the optical fiber may extend distal one or more fluid infusion openings in the elongate tubular member. A light may be applied through the optical fibers to particles in the tubular lumen, where the particles in the tubular lumen flow pass a distal end of the optical fiber. Light reflected by the particles in the tubular lumen may then be received or detected by the optical fiber. In some cases, the light may be emitted and/or received before, after, and/or while dispersing a fluid from the elongate tubular member into the tubular lumen at a known flow rate. A first measure of a number particles passing the optical fiber per unit time and a second measure of a number of particles passing the optical fiber per unit time may be obtained when a fluid is dispersed into the tubular lumen at a first known flow rate and when a fluid is dispersed into the tubular lumen at a second known flow rate, respectively. From these measures and/or other measures, an absolute flow rate of fluid and/or absolute flow restriction in the tubular lumen may be determined in accordance with the math described above.

Although particular method features may be described herein in particular orders, it is contemplated that the features of the disclosed methods may be performed in other orders and the orders presented are merely illustrative. Additionally, the method features disclosed herein may be performed by human operation, one or more computing devices (e.g., a device comprising a memory and processor for processing instructions saved in the memory), or with a combination of human operation and one or more computing devices.

Those skilled in the art will recognize that aspects of the present disclosure may be manifested in a variety of forms other than the specific embodiments described and contemplated herein. Accordingly, departure in form and detail may be made without departing from the scope and spirit of the present disclosure as described in the appended claims.

What is claimed is:

1. A system for determining fluid flow rate in a body lumen, the system comprising:
   a catheter including:
      a first lumen;
      a second lumen;
      a fluid infusion opening in communication with the first lumen and located at a distal end region of the catheter, the fluid infusion opening is configured to permit fluid to exit the catheter from the first lumen;
      an opening in communication with the second lumen and located at the distal end region of the catheter;
   an optical fiber having a reflective surface at a distal end thereof, wherein the optical fiber is advanceable through the second lumen of the catheter and positionable distal of the opening in communication with the second lumen; and
   wherein the reflective surface is substantially transparent to one or more wavelengths of light and the optical fiber is configured to receive light reflecting from particles in the body lumen to determine a flow rate of fluid in the body lumen.

2. The system of claim 1, further comprising:
   a beam splitter in communication with the optical fiber, wherein the beam splitter separates light reflected by the reflective surface from light reflected by particles flowing in the body lumen.

3. The system of claim 1, further comprising:
   a receiving detector for measuring reflected light received in the optical fiber.

4. The system of claim 1, further comprising:
   a Fabry-Perrot cell at the distal end of the optical fiber, wherein the reflective surface is a diaphragm of the Fabry-Perrot cell.

5. The system of any of claim 1, further comprising:
   a metal tube affixed to a distal end of the optical fiber and extending past a distal end of the optical fiber; and
   a diaphragm covering a distal opening of the metal tube.

6. The system of claim 5, wherein a space between the distal end of the optical fiber and the diaphragm forms a Fabry-Perrot cavity.

7. The system of claim 1, further comprising:
   one or more light reflecting surfaces positioned at a distal end of the catheter.

8. The system of any one of claim 7, wherein the light reflecting surfaces are positioned on the catheter at a position configured to reflect light toward the optical fiber.

9. A system for determining fluid flow rate in a body lumen, the system comprising:
   a catheter including:
      a first lumen;
      a second lumen;
      a fluid infusion opening in communication with the first lumen and located at a distal end region of the catheter, the fluid infusion opening is configured to permit fluid to exit the catheter from the first lumen;
      an opening in communication with the second lumen and located at the distal end region of the catheter;
   an optical fiber, wherein the optical fiber is positionable in the second lumen of the catheter and positionable distal of the opening in communication with the second lumen; and
   wherein a distal end of the optical fiber is substantially transparent to one or more wavelengths of light and the optical fiber is configured to receive light reflecting from particles in the body lumen to determine a flow rate of fluid in the body lumen.

10. The system of claim 9, further comprising:
    a beam splitter in communication with the optical fiber, wherein the beam splitter separates light reflected by particles flowing in the body lumen from other light.

11. The system of claim 9, further comprising:
    a receiving detector for measuring reflected light received in the optical fiber.

12. The system of claim 9, further comprising:
    a Fabry-Perrot cell at the distal end of the optical fiber, wherein the Fabry-Perrot cell includes a diaphragm having a reflective surface transparent to the one or more wavelengths of light.

13. The system of any of claim 10, further comprising:
    a metal tube affixed to the distal end of the optical fiber and extending past the distal end of the optical fiber; and
    a diaphragm covering a distal opening of the metal tube.

14. The system of claim 13, wherein a space between the distal end of the optical fiber and the diaphragm forms a Fabry-Perrot cavity.

15. The system of claim 9, further comprising:
    one or more light reflecting surfaces positioned at a distal end of the catheter.

16. The system of any one of claim 15, wherein the light reflecting surfaces are positioned on the catheter at a position configured to reflect light toward the optical fiber.

* * * * *